US 9,220,780 B2

(12) United States Patent
Jung et al.

(10) Patent No.: US 9,220,780 B2
(45) Date of Patent: *Dec. 29, 2015

(54) PHARMACEUTICAL LIQUID COMPOSITION OF BOTULINUM TOXIN WITH IMPROVED STABILITY

(71) Applicant: MEDY-TOX, INC., Chungcheongbuk-do (KR)

(72) Inventors: Hyun Ho Jung, Seoul (KR); Gi Hyeok Yang, Chungcheongnam-do (KR); Hack Woo Kim, Chungcheongbuk-do (KR); Hee Dong Woo, Chungcheongbuk-do (KR); Chang Hoon Rhee, Seoul (KR)

(73) Assignee: Medy-Tox Inc. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/088,821

(22) Filed: Nov. 25, 2013

(65) Prior Publication Data

US 2014/0161783 A1    Jun. 12, 2014

Related U.S. Application Data

(63) Continuation of application No. 12/666,592, filed as application No. PCT/KR2008/002975 on May 28, 2008, now Pat. No. 8,617,568.

(30) Foreign Application Priority Data

Jul. 10, 2007  (KR) .................... 10-2007-0069363

(51) Int. Cl.
| *A61K 38/48* | (2006.01) |
| *A61K 39/08* | (2006.01) |
| *A61K 47/22* | (2006.01) |
| *A61K 9/00* | (2006.01) |
| *A61K 47/18* | (2006.01) |
| *A61K 47/26* | (2006.01) |

(52) U.S. Cl.
CPC ............ *A61K 47/22* (2013.01); *A61K 9/0019* (2013.01); *A61K 38/4893* (2013.01); *A61K 47/183* (2013.01); *A61K 47/26* (2013.01)

(58) Field of Classification Search
CPC ........... A61K 38/48; A61K 9/00; A61K 9/19; A61K 39/08
USPC ................................ 424/234.1, 204.1, 184.1
See application file for complete search history.

(56) References Cited

U.S. PATENT DOCUMENTS

| 5,358,708 | A | * | 10/1994 | Patel | 424/85.1 |
| 5,656,730 | A | | 8/1997 | Lee | |
| 5,756,468 | A | | 5/1998 | Johnson et al. | |
| 5,763,395 | A | | 6/1998 | Blackburn et al. | |
| 5,871,736 | A | | 2/1999 | Bruegger et al. | |
| 7,354,740 | B2 | * | 4/2008 | Xiang et al. | 435/71.1 |
| 7,399,607 | B2 | | 7/2008 | Williams et al. | |
| 7,758,873 | B2 | | 7/2010 | Hunt | |
| 7,780,967 | B2 | * | 8/2010 | Hunt | 424/236.1 |
| 7,829,525 | B2 | * | 11/2010 | Frevert | 514/13.7 |
| 8,168,206 | B1 | * | 5/2012 | Hunt | 424/247.1 |
| 8,216,591 | B2 | * | 7/2012 | Hunt | 424/247.1 |
| 8,323,622 | B2 | * | 12/2012 | Kwon et al. | 424/9.6 |
| 8,323,666 | B2 | | 12/2012 | Hunt | |
| 8,617,568 | B2 | * | 12/2013 | Jung et al. | 424/197.11 |
| 8,642,047 | B2 | * | 2/2014 | Hunt | 424/234.1 |
| 8,920,795 | B2 | * | 12/2014 | Jung et al. | 424/94.67 |
| 8,993,268 | B2 | * | 3/2015 | Jung et al. | 435/71.3 |
| 2003/0138437 | A1 | * | 7/2003 | Hunt | 424/184.1 |
| 2005/0208076 | A1 | | 9/2005 | Hunt | |
| 2005/0238669 | A1 | * | 10/2005 | Xiang et al. | 424/239.1 |
| 2005/0241652 | A1 | * | 11/2005 | Hanin et al. | 128/898 |
| 2005/0276823 | A1 | * | 12/2005 | Cini et al. | 424/400 |
| 2006/0002862 | A1 | * | 1/2006 | Truong-Le et al. | 424/46 |
| 2006/0063222 | A1 | | 3/2006 | Williams et al. | |
| 2006/0104994 | A1 | * | 5/2006 | Hunt | 424/239.1 |
| 2006/0269575 | A1 | * | 11/2006 | Hunt | 424/239.1 |
| 2007/0026019 | A1 | * | 2/2007 | Hunt | 424/239.1 |
| 2007/0134199 | A1 | * | 6/2007 | Frevert | 424/85.4 |
| 2007/0264355 | A1 | * | 11/2007 | Allen et al. | 424/615 |
| 2009/0291062 | A1 | * | 11/2009 | Fraunhofer et al. | 424/85.5 |
| 2009/0324647 | A1 | * | 12/2009 | Borodic | 424/239.1 |
| 2010/0150994 | A1 | * | 6/2010 | Kotyla | 424/449 |
| 2010/0279953 | A1 | * | 11/2010 | Hunt | 514/21.2 |

(Continued)

FOREIGN PATENT DOCUMENTS

| CN | 1826132 A | 8/2006 |
| EP | 1 398 038 | 1/2007 |

(Continued)

*Primary Examiner* — Albert Navarro
*Assistant Examiner* — Ginny Portner
(74) *Attorney, Agent, or Firm* — Ted A. Chan

(57) ABSTRACT

Disclosed herein is a liquid pharmaceutical composition of botulinum toxin which is improved in stability. It comprises botulinum toxin, polysorbate 20, and methionine and optionally isoleucine. Employing, instead of the animal-derived protein albumin or gelatin, a combination of polysorbate 20 and methionine and optionally isoleucine as botulinum toxin stabilizers, the liquid pharmaceutical composition eliminates the risk of contaminating the body with serum-derived pathogens or microorganisms and can be administered safely to the body. Also, the composition is convenient for use as a direct injection for patients. Superior to conventional compositions employing either detergents or amino acids in terms of the storage stability of botulinum toxin at 25~37° C. as well as at refrigerated temperatures, the liquid pharmaceutical composition of the present invention is very useful for storing botulinum toxin under an emergency condition such as an environment without maintaining low temperature. The liquid pharmaceutical composition can be readily prepared because it employs a detergent and an amino acid(s) without a lyophilization process.

15 Claims, No Drawings

(56) References Cited

U.S. PATENT DOCUMENTS

| | | | |
|---|---|---|---|
| 2010/0291245 A1* | 11/2010 | Gao et al. | 424/729 |
| 2012/0302507 A1 | 11/2012 | Ham | |
| 2013/0287734 A1* | 10/2013 | Im et al. | 424/85.7 |
| 2014/0105882 A1* | 4/2014 | Taylor | 424/94.3 |
| 2014/0112908 A1* | 4/2014 | Hunt | 424/94.67 |
| 2015/0165003 A1* | 6/2015 | Jung et al. | A61K 39/08 |

FOREIGN PATENT DOCUMENTS

| | | | | |
|---|---|---|---|---|
| KR | 10-2006-0028475 | 3/2006 | | |
| KR | 10-2006-0090938 | 8/2006 | | |
| WO | 96/11699 | 4/1996 | | |
| WO | 97/35604 | 10/1997 | | |
| WO | 00/51629 | 9/2000 | | |
| WO | 01/58472 | 8/2001 | | |
| WO | 01/58472 A2 | 8/2001 | | |
| WO | 02/17957 | 3/2002 | | |
| WO | 2005/007185 | 1/2005 | | |
| WO | 2005/027954 | 3/2005 | | |
| WO | 2006/005910 | 1/2006 | | |
| WO | 2006/020208 | 2/2006 | | |
| WO | 2007/016018 | 2/2007 | | |
| WO | 2007/037607 | 4/2007 | | |
| WO | 2007/041664 | * | 4/2007 | A61K 9/00 |
| WO | 2009/008595 | * | 1/2009 | A61K 47/42 |

* cited by examiner

PHARMACEUTICAL LIQUID COMPOSITION OF BOTULINUM TOXIN WITH IMPROVED STABILITY

CROSS REFERENCE TO RELATED APPLICATION

The present application is a continuation of U.S. patent application Ser. No. 12/666,592, filed Jul. 27, 2010, now U.S. Pat. No. 8,617,568, which is a 35 U.S.C. §371 national phase application from, and claiming priority to, International Application PCT/KR2008/002975, filed May 28, 2008, and published under PCT Article 21(2) in English, which claims priority to Korean Application No. 10-2007-0069363, filed Jul. 10, 2007, which applications are incorporated by reference herein in their entireties.

TECHNICAL FIELD

The present invention relates, in general, to a more stable liquid pharmaceutical botulinum toxin composition and, more particularly, to a liquid pharmaceutical composition, comprising a botulinum toxin in combination with polysorbate 20 and methionine and optionally isoleucine.

BACKGROUND ART

Botulinum toxin is a neurotoxin protein produced by the bacterium *Clostridium botulinum*. This toxin blocks the presynaptic release of acetylcholine at the neuromuscular junction, causing flaccid (sagging) paralysis of muscles in mammals. The toxin has proven to be effective for treating strabismus, idiopathic blepharospasm and hemifacial spasm. In addition, it has recently been found to provide relief for a number of motor disturbances of involuntary muscles, including spasmodic torticollis, oromandibular dystonia, and spasmodic dyphonia. Further, botulinum toxin received FDA approval for temporary improvement in the facial appearance of moderate-to-severe frown lines and for the non-surgical treatment of hyperhidrosis (excessive underarm sweating).

The botulinum toxin proteins serotype A and B are now formulated into dosage forms for use in medical applications such as the treatment of torticollis, blepharospasm, hyperhidrosis, etc. as well as in cosmetic applications such as wrinkle reduction. Protein drugs, including botulinum toxin proteins, however, suffer from many problems during the preparation thereof. The problems, most of which are attributed to protein instability, are particularly pronounced for the protein drugs which are formulated with very low concentrations of active proteins, such as botulinum toxins.

Adhesing themselves onto solid surfaces, botulinum toxin proteins, when incased in vessels, are apt to adhere to the inner walls of the vessels, resulting in a loss of the active ingredient. A stabilizing agent is also required for preventing the proteins from being oxidized or degraded into fragments.

Albumin is selected in most cases for use as a stabilizer in the formulation of botulinum toxin. In addition to stabilizing the active protein ingredients in pharmaceutical compositions, albumin enjoys the advantage of showing negligible immunogenicity even when injected into the body. However, serum products such as albumin are not completely free from the possibility of being contaminated with pathogens or microorganisms and thus acting as mediators of disease, particularly viral diseases or Creutzfeldt-Jakob disease.

Often, gelatin is employed in place of albumin. Gelatin, however, is recommended not to be used as a stabilizer for drug formulation because this protein, similarly to albumin, is also obtained from animals and may mediate diseases.

A stabilizer derived from non-animal sources is provided for the pharmaceutical formulation of botulinum toxin by Korean Patent No. 10-0799400 in which recombinant serum albumin (rSA), produced in yeast, is applied for pharmaceutical formulation. However, complete avoidance cannot be provided to the possibility that a neoepitope, a new antigenic structure, may be generated in the course of the production, isolation and recovery of recombinant serum albumin (rSA), eliciting an immune response from the recipient of the drug. Korean Patent No. 10-0665469 discloses a pharmaceutical composition comprising a botulinum toxin, polysaccharides (including hydroxyethyl starch) and an amino acid such as lysine, glycine, histidine or arginine. This pharmaceutical composition is provided in a dosage form prepared by lyophylization and must unfortunately be stored at low-temperature in a refrigerator or freezer. The requirement that the lyophilized botulinum toxin be thawed or diluted just before use may cause an error in the protein. In addition to being inconvenient for use, lyophilized botulinum toxins are difficult to develop into a pre-filled syringe administration type.

A composition for stabilization of protein agents in pharmaceuticals is suggested by U.S. Patent Publication No. 2007-0134199. The composition comprises a non-ionic detergent, preferably polysorbate, and a combination of either glutamine and glutamic acid or asparagine and aspartic acid. A dilution of botulinum toxin in the liquid composition was observed to be stable for 8 months when stored at 4° C. However, because storage at 37° C. decreased the activity of the dilution within one month, the composition has limited use for the stabilization of protein agents, such as botulinum toxin, in pharmaceuticals to be stored at room temperature. This deficit is, in the opinion of the present inventors, attributed to the presence of the polar amino acids and particularly the acidic amino acids such as glutamic acid or aspartic acid.

DISCLOSURE OF INVENTION

Technical Problem

Accordingly, the present invention has been made keeping in mind the above problems occurring in the prior art, and an object of the present invention is to provide a pharmaceutical composition which can maintain the activity of botulinum toxin even after being stored for a long period of time at room temperature as well as at a refrigerated temperature and is in a liquid form more convenient for use than a lyophilized form.

It is another object of the present invention to provide a liquid pharmaceutical composition in which the activity of botulinum toxin can be stably maintained under a refrigerated or high temperature condition with the use of neither animal-derived protein, such as albumin or gelatin, as a stabilizer for botulinum toxin nor polar or acidic amino acids such as glutamine, glutamic acid, asparagine or aspartic acid.

Technical Solution

Leading to the present invention, intensive and thorough research, conducted by the present inventors with many detergents and amino acids, into the stable preservation of botulinum toxin under a high-temperature condition resulted in the finding that a combination of polysorbate 20 and methionine and optionally isoleucine is able to greatly improve the stability of botulinum toxin at room temperature or higher.

In accordance with an aspect of the present invention, there is provided a liquid pharmaceutical composition comprising botulinum toxin, polysorbate 20, and methionine.

In accordance with another aspect of the present invention, there is provided a liquid pharmaceutical composition comprising botulinum toxin, polysorbate 20, methionine and isoleucine.

In the liquid pharmaceutical composition, the methionine is present in an amount of 0.5 to 100 μmol per 100 units of botulinum toxin, and preferably ranges in concentration from 0.5 to 100 mM and more preferably from 25 to 75 mM.

In the liquid pharmaceutical composition according to the present invention, polysorbate 20 is present in an amount of 0.01 to 50 mg per 100 units of botulinum toxin and preferably ranges in concentration from 0.01 to 50 mg/mL and more preferably form 0.1 to 2.5 mg/mL.

In the liquid pharmaceutical composition according to the present invention, the botulinum toxin is selected from a group consisting of botulinum toxin serotypes A, B, C, D, E, F, and G and may be in a non-complex form or in a complex form with a protein. Preferably, the botulinum toxin ranges in concentration from 50 to 5,000 units/mL.

The liquid pharmaceutical composition according to the present invention preferably ranges in pH from 5.5 to 7.0.

Advantageous Effects

Employing as botulinum toxin stabilizers, instead of the animal-derived protein albumin or gelatin, a combination of polysorbate 20 and methionine, optionally with isoleucine, the liquid pharmaceutical composition according to the present invention eliminates the risk of contaminating the body with serum-derived pathogens or microorganisms and can be administered safely.

In addition, the liquid pharmaceutical composition of the present invention can be convenient for use as a direct injection for patients. Furthermore, as well as at refrigerated temperatures, in terms of the storage stability of botulinum toxin at 25~37° C., the liquid pharmaceutical composition of the present invention is very useful for storing botulinum toxin under an emergency condition such as an environment without maintaining low temperature, thus being superior to conventional liquid pharmaceutical compositions employing either detergents or amino acids.

The liquid pharmaceutical composition of the present invention can be readily prepared because it employs a detergent and an amino acid(s) without a lyophilization process.

BEST MODE FOR CARRYING OUT THE INVENTION

A liquid pharmaceutical composition with improvement in botulinum stability is provided in accordance with the present invention. Particularly, the liquid pharmaceutical composition comprises a botulinum toxin, polysorbate 20 and methionine and optionally isoleucine.

The liquid pharmaceutical composition comprising a botulinum toxin, polysorbate 20 and methionine, or alternatively, a botulinum toxin, polysorbate 20, methionine and isoleucine in accordance with the present invention is much improved in botulinum toxin stability.

With the employment of polysorbate 20, methionine and optionally isoleucine, instead of an animal-derived protein such as albumin or gelatin, as stabilizers for botulinum toxin, the liquid pharmaceutical composition of the present invention excludes the potential risk of infecting the recipient with serum-derived pathogens or microorganisms and is thus safe for ingestion into the body. In addition, the use of the stabilizers polysorbate 20, methionine and optionally isoleucine in combination guarantees higher stability to botulinum toxin at 25~27° C. than does the use of them in a separate manner.

The botulinum toxin, a constituent of the liquid pharmaceutical composition according to the present invention, may be one selected from among serotypes A, B, C, D, E, F and G. The term botulinum toxin is a generic term embracing the family of toxins produced by the anaerobic bacterium *Clostridium botulinum* and, to date, seven immunologically distinct neurotoxins serotypes have been identified. These have been given the designations A, B, C, D, E, F and G, which differ one from the other in their effects on target animals, and paralysis extent and duration. All serotypes of botulinum toxin are known to act as a neurotoxin by inhibiting the neurotransmitter acetylcholine at neuromuscular junctions.

The botulinum toxin of the liquid pharmaceutical composition according to the present invention may be in a non-complex form or in a complex form with another protein. Botulinum toxin serotype A, B, C, D, E, F or G alone, synthesized by *Clostridium botulinum*, itself has a molecular weight of approximately 150 kDa. When expressed in *Clostridium botulinum*, the botulinum toxin forms various complexes with hemagglutinin proteins and non-hemagglutinin proteins which aid and protect the activity thereof. Naturally occurring botulinum type A complexes have a molecular weight of approximately 900 kDa, 500 kDa or 300 kDa. Molecular weights are measured to be approximately 500 kDa for botulinum toxin type B complexes and type C complexes, approximately 300 kDa or 500 kDa for type D complexes, and approximately 300 kDa for type E and type F complexes.

Although not severely restricted, the concentration of the botulinum toxin in the liquid pharmaceutical composition of the present invention preferably ranges from 50 to 5,000 units/mL depending on the general use thereof.

Methionine is present in an amount from 0.5 to 100 μmol per 100 units of botulinum toxin, and preferably ranges in concentration from 0.5 to 100 mM and more preferably from 25 to 75 mM in the liquid pharmaceutical composition of the present invention.

One unit (U) of botulinum toxin is defined as the $LD_{50}$ upon intraperitoneal injection into female Swiss Webster mice weighing 18~20 grams each. The $LD_{50}$ of botulinum toxin in mice corresponds to about 50 picograms.

A methionine content less than 0.5 μmol per 100 units of botulinum toxin cannot guarantee the stabilization of the botulinum toxin to a desirable level upon long-term storage at room temperature. On the other hand, when methionine is used in an amount exceeding 100 μmol per 100 units of botulinum toxin, the excess increment may not promise an additional stabilization effect in addition to incurring an economic disadvantage. In the liquid pharmaceutical composition of the present invention, methionine properly ranges in concentration from 0.5 to 100 mM when the botulinum toxin has a concentration of 100 units/mL. Its proper concentration is adjusted to 25-75 mM in consideration of the concentration range of polysorbate 20. When the concentration of methionine is below 25 mM in the liquid pharmaceutical composition of the present invention, its long-term stabilization effect on botulinum toxin at room temperature does not reach the desirable level, which is obtainable in the proper concentration range of botulinum toxin. On the other hand, a methionine concentration exceeding 75 mM does not provide any additional effect.

In the liquid pharmaceutical composition of the present invention, polysorbate 20 is present in an amount of 0.01 to 50 mg per 100 units of botulinum toxin and preferably ranges in concentration from 0.01 to 50 mg/mL and more preferably form 0.1 to 2.5 mg/mL.

Polysorbates are a class of emulsifiers used in some pharmaceuticals and in food preparation. They are often used in cosmetics to dissolve essential oils into waterbased (oil-in-water) products. There are many kinds of polysorbates that are classified by a number referring to the total number of oxyethylene groups, such as polysorbate 20, 40, 60 and 80. The liquid pharmaceutical composition of the present invention employs polysorbate 20 (commercially available as brand name Tween 20) as a stabilizer for botulinum toxin.

If the liquid pharmaceutical composition of the present invention contains polysorbate 20 in an amount less than 0.01 mg per 100 units of botulinum toxin, its long-term stabilization effect on botulinum toxin at room temperature does not reach a desirable level. On the other hand, a polysorbate 20 concentration exceeding 50 mg/mL does not provide any additional effect in addition to incurring an economic disadvantage. At a concentration of 100 units/mL of botulinum toxin in the liquid pharmaceutical composition of the present invention, polysorbate 20 is properly present in an amount of 0.01~50 mg/mL and preferably in an amount of 0.1~2.5 mg/mL when the methionine concentration is taken into consideration. When the concentration of polysorbate 20 in the liquid pharmaceutical composition of the present invention is less than 0.1 mg/mL, its long-term stabilization effect on botulinum toxin at room temperature does not reach a desired level, which is obtainable by the target concentration of polysorbate 20. On the other hand, a polysorbate 20 concentration exceeding 2.5 mg/mL does not provide any additional effect.

In accordance with the present invention, the liquid pharmaceutical composition has a pH of 5.5~7.0. In the liquid pharmaceutical composition of the present invention adjusted to a pH of 5.5~7.0, botulinum toxin is stably maintained at room temperature (particularly 40° C.) for a long period of time.

MODE FOR THE INVENTION

A better understanding of the present invention may be obtained through the following examples which are set forth to illustrate, but are not to be construed as the limit of the present invention.

1. Experiment Method (1) Preparation of Liquid Botulinum Toxin Composition

A botulinum toxin was diluted to a final concentration of 100 units/mL in a stabilizing solution.

(2) Stability Assay of Botulinum Toxin

While the prepared liquid botulinum toxin composition was stored at a certain temperature, samples of 1 mL were taken therefrom at predetermined intervals. 1 mL of the sampled liquid composition was 10-fold diluted using 9 mL of an injection solution. The diluted sample was intraperitoneally injected into five female ICRmice (Institute of Cancer Research, USA) (at a dose of 0.3 mL per mouse, that is, 3 units/mouse). While the mice were observed 3 days after the intraperitoneal injection, the death toll and mortalityrate were analyzed. The liquid botulinum toxin composition was evaluated for maintenance of the activity of botulinum toxin when the mortality rate was 50% or higher.

2. Selection of Botulinum Toxin Stabilizer liquid botulinum toxin compositions containing Various candidates of botulinum toxin stabilizer were prepared and analyzed for botulinum toxin stability over time during storage at 25° C. or 37° C. Results of the stability experiments at 25° C. and 37° C. are summarized in Tables 1 and 2, respectively. In Tables 1 and 2, HSA stands for human serum albumin and PEG8000 represents polyethylene glycol 8000.

At 25° C., as seen in Table 1, the activity of botulinum toxin was maintained for a long period of time in a liquid composition comprising L-methione (20 mM)+polysorbate20 (2 mg/mL)+botulinum toxin (100 units/mL), HSA (5 mg/mL)+polysorbate 20 (2 mg/mL)+botulinum toxin (100 units/mL), L-Isoleucine (50 mM)+polysorbate 20 (2 mg/mL)+botulinum toxin (100 units/mL), a hydroxyethyl starch (10 mg/mL)+polysorbate 20 (2 mg/mL)+botulinum toxin (100 units/mL). At 37° C., the liquid composition comprising L-methione (20 mM)+polysorbate 20 (2 mg/mL)+botulinum toxin (100 units/mL) or HSA (5 mg/mL)+polysorbate 20 (2 mg/mL)+botulinum toxin (100 units/mL) was found to maintain the activity of botulinum toxin for a long period of time as seen in Table 2.

From the results, it is recognized that a combination of methionine and polysorbate 20 acts as a stabilizer substitutable for a combination of HSA and polysorbate 20 or a combination of hydroxyethyl starch and polysorbate 20. Also, a combination of isoleucine and polysorbate 20 emerged as a stabilizer candidate substitutable for conventional stabilizers.

TABLE 1

| | Botulinum Toxin Composition | | | | | | | |
|---|---|---|---|---|---|---|---|---|
| Ex. Nos. | Stabilizer (Conc.) | PolySor 20(mg/mL) | B. toxin (Units/mL) | Mortality rate(%) | | | | |
| | | | | Day 0 | Day 6 | Day 14 | Day 23 | Day 35 |
| 1 | L-Met (20 mM) | 2.0 | 100 | 100 | 100 | 100 | 100 | 100 |
| C. 1 | — | 2.0 | 100 | 100 | 0 | — | — | — |
| C. 2 | HAS(5 mg/mL) | — | 100 | 100 | 100 | 0 | — | — |
| C. 3 | HAS(5 mg/mL) | 2.0 | 100 | 100 | 100 | 100 | 100 | 100 |
| C. 4 | L-Arg(50 mM) | 2.0 | 100 | 100 | 0 | — | — | — |
| C. 5 | L-Ile(50 mM) | 2.0 | 100 | 100 | 80 | 100 | 60 | 80 |
| C. 6 | L-Glu(50 mM) | 2.0 | 100 | 100 | 100 | 0 | — | — |
| C. 7 | His(10 mM) | 2.0 | 100 | 100 | 0 | — | — | — |
| C. 8 | Glu(8 mg/ml) | 2.0 | 100 | 100 | 100 | 60 | 0 | — |
| C. 9 | Gly(2 mg/ml) | 2.0 | 100 | 100 | 0 | — | — | — |
| C. 10 | Na Glm(10 mM) | 2.0 | 100 | 100 | 100 | 0 | — | — |
| C. 11 | Hydroxyethyl Starch(10 mg/ml) | 2.0 | 100 | 100 | 100 | 80 | 80 | 60 |
| C. 12 | Mannitol (50 mg/ml) | 2.0 | 100 | 100 | 0 | — | — | — |
| C. 13 | Sorbitol (50 mg/ml) | 2.0 | 100 | 100 | 60 | 0 | — | — |
| C. 14 | C8-Glucose (50 mg/ml) | 2.0 | 100 | 100 | 0 | — | — | — |

TABLE 1-continued

| Ex. Nos. | Botulinum Toxin Composition Stabilizer (Conc.) | PolySor 20(mg/mL) | B. toxin (Units/mL) | Mortality rate(%) |  |  |  |  |
|---|---|---|---|---|---|---|---|---|
|  |  |  |  | Day 0 | Day 6 | Day 14 | Day 23 | Day 35 |
| C. 15 | C8-Trehalose (50 mg/ml) | 2.0 | 100 | 100 | 0 | — | — | — |
| C. 16 | Sucrose (50 mg/ml) | 2.0 | 100 | 100 | 0 | — | — | — |
| C. 17 | Lactose (50 mg/ml) | 2.0 | 100 | 100 | 0 | — | — | — |
| C. 18 | PEG8000 (100 mg/ml) | 2.0 | 100 | 100 | 0 | — | — | — |
| C. 19 | Hyaluronic acid (10 mg/ml) | 2.0 | 100 | 100 | 0 | — | — | — |

TABLE 2

| Ex. Nos. | Botulinum Toxin Composition Stabilizer (Conc.) | PolySor 20(mg/mL) | B. toxin (Units/mL) | Mortality rate(%) |  |  |  |  |
|---|---|---|---|---|---|---|---|---|
|  |  |  |  | Day 0 | Day 6 | Day 14 | Day 23 | Day 35 |
| 1 | L-Met (20 mM) | 2.0 | 100 | 100 | 100 | 100 | 100 | 100 |
| C. 1 | — | 2.0 | 100 | 100 | 0 | — | — | — |
| C. 2 | HAS(5 mg/mL) | — | 100 | 100 | 100 | 0 | — | — |
| C. 3 | HAS(5 mg/mL) | 2.0 | 100 | 100 | 100 | 80 | 100 | 100 |
| C. 4 | L-Arg(50 mM) | 2.0 | 100 | 100 | 0 | — | — | — |
| C. 5 | L-Ile(50 mM) | 2.0 | 100 | 100 | 0 | — | — | — |
| C. 6 | L-Glu(50 mM) | 2.0 | 100 | 100 | 0 | — | — | — |
| C. 7 | His(10 mM) | 2.0 | 100 | 100 | 0 | — | — | — |
| C. 8 | Glu(8 mg/ml) | 2.0 | 100 | 100 | 0 | — | — | — |
| C. 9 | Gly(2 mg/ml) | 2.0 | 100 | 100 | 0 | — | — | — |
| C. 10 | Na Glm(10 mM) | 2.0 | 100 | 100 | 0 | — | — | — |
| C. 11 | Hydroxyethyl Starch(10 mg/ml) | 2.0 | 100 | 100 | 100 | 0 | — | — |
| C. 12 | Mannitol (50 mg/ml) | 2.0 | 100 | 100 | 0 | — | — | — |
| C. 13 | Sorbitol (50 mg/ml) | 2.0 | 100 | 100 | 0 | — | — | — |
| C. 14 | C8-Glucose (50 mg/ml) | 2.0 | 100 | 100 | 0 | — | — | — |
| C. 15 | C8-Trehalose (50 mg/ml) | 2.0 | 100 | 100 | 0 | — | — | — |
| C. 16 | Sucrose (50 mg/ml) | 2.0 | 100 | 100 | 0 | — | — | — |
| C. 17 | Lactose (50 mg/ml) | 2.0 | 100 | 100 | 0 | — | — | — |
| C. 18 | PEG8000 (100 mg/ml) | 2.0 | 100 | 100 | 0 | — | — | — |
| C. 19 | Hyaluronic acid (10 mg/ml) | 2.0 | 100 | 100 | 0 | — | — | — |

3. Stability of Botulinum Toxin at Various Concentrations of Methionine

Liquid botulinum toxin compositions comprising various concentrations of methionine in combination with polysorbate 20 as botulinum toxin stabilizers were assayed for ability to maintain the activity of botulinum toxin under a 37° C. storage condition. The experimental results of the stability of botulinum toxin according to a change in methionine concentration are summarized in Table 3, below.

TABLE 3

| Ex. Nos. | Botulinum Toxin Composition |  |  | Mortality rate(%) Day |  |  |  |  |  |  |  |
|---|---|---|---|---|---|---|---|---|---|---|---|
|  | Met (mM) | PolySor 20(mg/mL) | B. toxin (Units/mL) | 4 | 10 | 18 | 24 | 29 | 44 | 56 | 70 |
| 2 | 0.5 | 2.0 | 100 | 100 | 100 | 100 | 100 | 100 | 100 | 60 | 0 |
| 3 | 1.0 | 2.0 | 100 | 100 | 100 | 100 | 100 | 100 | 100 | 100 | 100 |
| 4 | 20 | 2.0 | 100 | 100 | 100 | 100 | 100 | 100 | 100 | 100 | 0 |
| 5 | 50 | 2.0 | 100 | 100 | 100 | 100 | 100 | 100 | 100 | 100 | 100 |

TABLE 3-continued

| Ex. Nos. | Botulinum Toxin Composition | | | Mortality rate(%) Day | | | | | | | |
|---|---|---|---|---|---|---|---|---|---|---|---|
| | Met (mM) | PolySor 20(mg/mL) | B. toxin (Units/mL) | 4 | 10 | 18 | 24 | 29 | 44 | 56 | 70 |
| 6 | 100 | 2.0 | 100 | 100 | 100 | 100 | 100 | 100 | 100 | 100 | 100 |
| C. 20 | — | 2.0 | 100 | 0 | — | — | — | — | — | — | — |

As seen in Table 3, the activity of botulinum toxin was stably maintained for 56 days at a methionine concentration of 0.5~20 mM and for 70 days at a methionine concentration of 50~100 mM. The composition employing both methionine and polysorbate 20 greatly improved the stability of botulinum toxin as compared with the composition employing polysorbate 20 alone.

4. Stability of Botulinum Toxin at Various Concentrations of Polysorbate 20

Liquid botulinum toxin compositions comprising methionine in combination with various concentrations of polysorbate 20 as botulinum toxin stabilizers were assayed for ability to maintain the activity of botulinum toxin under a 37° C. storage condition. The experimental results of the stability of botulinum toxin according to a change in polysorbate concentration are summarized in Table 4, below.

TABLE 4

| Ex. Nos. | Botulinum Toxin Composition | | | Mortality rate(%) Day | | | | | |
|---|---|---|---|---|---|---|---|---|---|
| | Met (mM) | PolySor 20(mg/mL) | B. toxin (Units/mL) | 30 | 60 | 90 | 120 | 167 | 202 |
| 7 | 20 | 0.01 | 100 | 100 | 100 | 100 | 100 | 80 | 0 |
| 8 | 20 | 0.5 | 100 | 100 | 80 | 100 | 100 | 80 | 100 |
| 9 | 20 | 2.0 | 100 | 100 | 100 | 80 | 100 | 80 | 100 |
| 10 | 20 | 10 | 100 | 100 | 100 | 80 | 100 | 40 | 0 |
| 11 | 20 | 50 | 100 | 100 | 0 | — | — | — | — |
| C. 21 | 1 | — | 100 | 0 | — | — | — | — | — |
| C. 22 | 5 | — | 100 | 0 | — | — | — | — | — |
| C. 23 | 10 | — | 100 | 0 | — | — | — | — | — |
| C. 24 | 20 | — | 100 | 0 | — | — | — | — | — |

As seen in Table 4, the activity of botulinum toxin was stably maintained for 202 days at a polysorbate 20 concentrations of 0.5~2.0 mg/mL, for 167 days at a polysorbate 20 concentration of 0.01 mg/mL and for 120 days at a polysorbate 20 concentration of 10 mg/mL. The composition employing both methionine and polysorbate 20 was greatly improved in the stability of botulinum toxin as compared with the composition employing methionine alone.

5. Stability of Botulinum Toxin at Various Concentrations of Methionine and Polysorbate 20

Liquid botulinum toxin compositions comprising various concentrations of a combination of methionine and polysorbate 20 as botulinum toxin stabilizers were assayed for their ability to maintain the activity of botulinum toxin under a 37° C. storage condition. The experimental results (mortality rate, %) of the stability of botulinum toxin after storage for 30 and 60 days at various concentrations of methionine and polysorbate 20 (Example 12) are summarized in Tables 5 and 6, respectively. In the liquid botulinum toxin compositions used in the experiments, botulinum toxin had a concentration of 100 units/mL.

Statistical analysis of the data of Tables 5 and 6 suggests that a combination of 25~75 mM of methionine and 0.1~2.5 mg/mL of polysorbate 20 stabilize botulinum toxin at highest efficiency.

TABLE 5

| Conc. Of Polysorbate 20/Met | | Met (mM) | | | | | | |
|---|---|---|---|---|---|---|---|---|
| | | 1 | 5 | 10 | 25 | 50 | 75 | 100 |
| Polysorbate 20 (mg/mL) | 0.1 | 100 | 100 | 80 | 100 | 100 | 100 | 100 |
| | 0.5 | 100 | 100 | 80 | 100 | 100 | 100 | 100 |
| | 2.5 | 100 | 100 | 100 | 100 | 100 | 100 | 100 |
| | 10 | 100 | 100 | 100 | 100 | 100 | 100 | 100 |
| | 25 | 100 | 100 | 100 | 100 | 100 | 100 | 100 |
| | 50 | 80 | 100 | 100 | 80 | 80 | 100 | 100 |

TABLE 6

| Conc. Of Polysorbate 20/Met | | Met (mM) | | | | | | |
|---|---|---|---|---|---|---|---|---|
| | | 1 | 5 | 10 | 25 | 50 | 75 | 100 |
| Polysorbate 20 (mg/mL) | 0.1 | 100 | 100 | 80 | 100 | 100 | 80 | 100 |
| | 0.5 | 100 | 100 | 80 | 100 | 100 | 100 | 100 |
| | 2.5 | 100 | 100 | 100 | 80 | 100 | 100 | 100 |
| | 10 | 0 | 40 | 0 | 100 | 100 | 100 | 40 |
| | 25 | 0 | 80 | 80 | 100 | — | 100 | 60 |
| | 50 | 0 | 0 | 0 | 0 | 80 | — | 0 |

6. Stability of Botulinum Toxin in Liquid Botulinum Toxin Compositions with Various pHs Various liquid botulinum toxin compositions (Example 13) with a pH of 5.5~7.0, in which methionine and polysorbate 20 were combined in their respective concentration ranges optimal for the stabilization of botulinum toxin, were prepared and assayed for ability to maintain the activity of botulinum toxin under a 40° C. storage condition. The pH of the liquid botulinum toxin compositions was adjusted with HCl or NaOH. Each of the compositions had a botulinum toxin concentration of 100 units/mL. The results of the stability of botulinum toxin according to the pH of the liquid composition are summarized in Table 7, below.

As seen in FIG. 7, the activity of botulinum toxin was stably maintained for 90 days in liquid botulinum toxin compositions containing of 25~75 mM of methionine in combination with 0.25~0.75 mg/mL of polysorbate 20 with the pH thereof ranging from 5.5 to 7.0 under a 40° C. storage condition.

TABLE 7

| Botulinum Toxin Composition | | | Mortality rate(%) | | | | |
|---|---|---|---|---|---|---|---|
| Met | PolySorbate20 | | Day | | | | |
| (mM) | (mg/mL) | pH | 7 | 15 | 30 | 60 | 90 |
| 25 | 0.25 | 5.5 | 100 | 100 | 100 | 100 | 100 |
| | | 6.0 | 100 | 100 | 100 | 100 | 100 |
| | | 6.5 | 100 | 100 | 100 | 100 | 100 |
| | | 7.0 | 100 | 100 | 100 | 100 | 100 |
| | 0.5 | 5.5 | 100 | 100 | 100 | 100 | 100 |
| | | 6.0 | 100 | 100 | 100 | 100 | 100 |
| | | 6.5 | 100 | 100 | 100 | 100 | 100 |
| | | 7.0 | 100 | 100 | 100 | 100 | 100 |
| | 0.75 | 5.5 | 100 | 100 | 100 | 100 | 100 |
| | | 6.0 | 100 | 100 | 100 | 100 | 100 |
| | | 6.5 | 100 | 100 | 100 | 100 | 100 |
| | | 7.0 | 100 | 100 | 100 | 100 | 100 |
| 50 | 0.25 | 5.5 | 100 | 100 | 100 | 100 | 100 |
| | | 6.0 | 100 | 100 | 100 | 100 | 100 |
| | | 6.5 | 100 | 100 | 100 | 100 | 100 |
| | | 7.0 | 100 | 100 | 100 | 100 | 100 |
| | 0.5 | 5.5 | 100 | 100 | 100 | 100 | 100 |
| | | 6.0 | 100 | 100 | 100 | 100 | 100 |
| | | 6.5 | 100 | 100 | 100 | 100 | 100 |
| | | 7.0 | 100 | 100 | 100 | 100 | 100 |
| | 0.75 | 5.5 | 100 | 100 | 100 | 100 | 100 |
| | | 6.0 | 100 | 100 | 100 | 100 | 100 |
| | | 6.5 | 100 | 100 | 100 | 100 | 100 |
| | | 7.0 | 100 | 100 | 100 | 100 | 100 |
| 75 | 0.25 | 5.5 | 100 | 100 | 100 | 100 | 100 |
| | | 6.0 | 100 | 100 | 100 | 100 | 100 |
| | | 6.5 | 100 | 100 | 100 | 100 | 100 |
| | | 7.0 | 100 | 100 | 100 | 100 | 100 |
| | 0.5 | 5.5 | 100 | 100 | 100 | 100 | 100 |
| | | 6.0 | 100 | 100 | 100 | 100 | 100 |
| | | 6.5 | 100 | 100 | 100 | 100 | 100 |
| | | 7.0 | 100 | 100 | 100 | 100 | 100 |
| | 0.75 | 5.5 | 100 | 100 | 100 | 100 | 100 |
| | | 6.0 | 100 | 100 | 100 | 100 | 100 |
| | | 6.5 | 100 | 100 | 100 | 100 | 100 |
| | | 7.0 | 100 | 100 | 100 | 100 | 100 |

7. Stability of Botulinum Toxin in Liquid Pharmaceutical Composition Containing a Combination of Methionine, Isoleucine and Polysorbate As described above, a combination of isoleucine and polysorbate 20 as well as a combination of methione and polysorbate 20 was identified as a candidate for stabilizing botulinum toxin. On the basis of this result, a combination of methionine, isoleucine and polysorbate 20 was assayed for ability to stabilize botulinum toxin under a 37° C. storage condition. In the liquid composition, botulinum toxin had a concentration of 100 units/mL.

TABLE 8

| | Botulinum Toxin Composition | | | Mortality rate(%) | | | | | |
|---|---|---|---|---|---|---|---|---|---|
| Ex. | Met | Ile | Polysorbate20 | Day | | | | | |
| Nos. | (mM) | (mg/mL) | (mg/mL) | 30 | 60 | 90 | 120 | 167 | 202 |
| 14 | 20 | 10 | 0.5 | 100 | 100 | 80 | 100 | 100 | 100 |
| 15 | 20 | 10 | 2.0 | 100 | 80 | 80 | 100 | 100 | 0 |
| 16 | 20 | 10 | 10 | 100 | 100 | 100 | 100 | 100 | 100 |
| C. 25 | — | 10 | — | 80 | 0 | — | — | — | — |
| C. 26 | 20 | 10 | — | 0 | — | — | — | — | — |
| C. 27 | — | 10 | 0.5 | 0 | — | — | — | — | — |
| C. 28 | — | 1 | 2.0 | 0 | — | — | — | — | — |
| C. 29 | — | 10 | 2.0 | 0 | — | — | — | — | — |
| C. 30 | — | 30 | 2.0 | 0 | — | — | — | — | — |
| C. 31 | — | 50 | 2.0 | 0 | — | — | — | — | — |
| C. 32 | — | 100 | 2.0 | 0 | — | — | — | — | — |
| C. 33 | — | 10 | 10 | 0 | — | — | — | — | — |

As seen in FIG. 8, the activity of botulinum toxin was maintained for a long period of time (approximately 200 days) under a 37° C. storage condition by a combination of methionine, isoleucine and polysorbate 20, but was found to almost disappear before the lapse of 30 days in the liquid compositions containing isoleucine alone or in combination with methionine or polysorbate 20.

INDUSTRIAL APPLICABILITY

As described hitherto, the liquid pharmaceutical botulinum toxin composition according to the present invention shows greatly improved botulinum toxin stability. It is useful in the treatment of dystonia, stiff muscle spasm, neurological disorders (migraine, lumbago, cervical spinal disorder, etc.) as well as in the cosmetic application for hyperhidrosis treatment and wrinkle reduction. In addition, the liquid pharmaceutical botulinum toxin composition of the present invention may be directly used as an injection and guarantees the activity of botulinum toxin for a long period of time even at 25~37° C. as well as at a refrigerated temperature, which is very advantageous for transportation and sale.

The invention claimed is:

1. A liquid pharmaceutical composition comprising botulinum toxin, polysorbate 20 and methionine, wherein the activity of the botulinum toxin is maintained after the composition is stored for at least 35 days at 25° C., wherein the composition is free of gelatin or human serum albumin, wherein the methionine is present at a concentration from 1 mM to 10 mM per 100 units of botulinum toxin and wherein the liquid pharmaceutical composition has not undergone a lyophilization process.

2. The liquid pharmaceutical composition of claim 1, wherein the methionine ranges in concentration from 1 to 5 mM.

3. The liquid pharmaceutical composition of claim 1, wherein the polysorbate 20 is present in an amount of 0.01 to 50 mg per 100 units of botulinum toxin.

4. The liquid pharmaceutical composition of claim 1, wherein the polysorbate 20 ranges in concentration from 0.01 to 50 mg/mL.

5. The liquid pharmaceutical composition of claim 1, wherein the botulinum toxin is selected from a group consisting of botulinum toxin serotypes A, B, C, D, E, F, and G.

6. The liquid pharmaceutical composition of claim 1, wherein the botulinum toxin is in a non-complex form or in a complex form with a protein.

7. The liquid pharmaceutical composition of claim 1, wherein the liquid pharmaceutical composition ranges in pH from 5.5 to 7.0.

8. The liquid pharmaceutical composition of claim 1, further comprising isoleucine.

9. The liquid pharmaceutical composition of claim 1, wherein the botulinum toxin ranges in concentration from 50 to 5,000 units/mL.

10. A liquid pharmaceutical composition comprising botulinum toxin, polysorbate 20 and methionine, wherein the methionine is present at a concentration from 1 mM to 10 mM, the polysorbate 20 is present in an amount, of from 0.1 to about 2.5 mg/ml per 100 units of botulinum toxin, wherein the composition is free of gelatin or human serum albumin; and wherein the liquid pharmaceutical composition has not undergone a lyophilization process.

11. The liquid pharmaceutical composition of claim 10, wherein the botulinum toxin is selected from a group consisting of botulinum toxin serotypes B, C, D, E, F, and G.

12. The liquid pharmaceutical composition of claim 10, wherein the botulinum toxin is in a non-complex form or in a complex form with a protein.

13. The liquid pharmaceutical composition of claim 10, wherein the liquid pharmaceutical composition ranges in pH from 5.5 to 7.0.

14. The liquid pharmaceutical composition of claim 10, further comprising isoleucine.

15. The liquid pharmaceutical composition of claim 10, wherein the botulinum toxin ranges in concentration from 50 to 5,000 units/mL.

* * * * *